United States Patent [19]

Rados

[11] Patent Number: 5,954,657
[45] Date of Patent: Sep. 21, 1999

[54] CAPTIVE DEADENDER FOR LUER FITTING

[76] Inventor: Stephen E. Rados, 207 Ashby Ct., Oak View, Calif. 93022

[21] Appl. No.: 08/808,132

[22] Filed: Feb. 28, 1997

Related U.S. Application Data

[63] Continuation of application No. 08/693,492, Aug. 2, 1996, abandoned, which is a continuation of application No. 08/561,213, Nov. 21, 1995, abandoned, which is a continuation of application No. 08/364,068, Dec. 27, 1994, abandoned, which is a continuation of application No. 08/073,851, Jun. 8, 1993, abandoned, which is a continuation of application No. 08/693,492, Aug. 2, 1996, abandoned.

[51] Int. Cl.$^6$ ........................................................ A61B 5/00
[52] U.S. Cl. ............................................. 600/486; 600/488
[58] Field of Search ..................... 315/320, 330, 315/334–6, 367; 400/486–488

[56] References Cited

U.S. PATENT DOCUMENTS

| | | |
|---|---|---|
| 3,815,769 | 6/1974 | Rapo et al. ............................. 215/354 |
| 4,682,700 | 7/1987 | Montgomery et al. .................. 215/330 |
| 4,936,474 | 6/1990 | Szczesniak et al. ..................... 215/330 |
| 5,147,052 | 9/1992 | Minette .................................... 215/330 |
| 5,228,583 | 7/1993 | Weinstein ................................ 215/330 |
| 5,297,599 | 3/1994 | Bucheli ................................... 215/364 |

*Primary Examiner*—Robert L. Nasser

[57] ABSTRACT

A captive deadender cap for use in venting the patient side chamber of a disposable pressure transducer through a vent port. The captive deadender cap includes retention tabs formed along the internal threads of the standard Luer threads of the deadender cap and which create a resistance with the mating external threads of the female Luer fitting on the vent port. Thus the captive deadender cap is not easily removable but is held captive to the vent port. By an increase in the torque, however, the resistance may be overcome by the user and, if desired, the captive deadender cap may be fully removed from the vent port.

4 Claims, 3 Drawing Sheets

CAPTIVE DEADENDER FOR LUER FITTING

This is a continuation of U.S. Ser. No. 08/693,492, file Aug. 2, 1996, now abandoned, which is continuation of application Ser. No. 08/561,213 filed Nov. 21, 1995 now abandoned, which in turn is a continuation of application Ser. No. 08/364,068 filed Dec. 27, 1994 now abandoned, which in turn is a continuation of Ser. No. 08/073,851 filed Jun. 8, 1993 now abandoned, which in turn is a continuation of Ser. No. 08/693,492 filed Aug. 2, 1996 now abandoned.

BACKGROUND OF THE INVENTION

This invention relates to disposable medical blood pressure measuring devices that are utilized with in vivo catheters to measure and record the blood pressure of a patient. Basically in vivo blood pressure monitoring is widely used in hospitals and includes a liquid filled catheter system that is introduced into the particular blood vessel to be monitored. The open end of the liquid filled catheter thus is placed within the patient's blood vessel and a continuous column of liquid takes up the space between that catheter end and a pressure transducer. The blood pressure may therefore be directly measured by the transducer remote from the patient by measuring the fluctuations of pressure at the external end of the liquid column.

Typically such pressure transducers comprise strain gauges in the form of cantilever beams for example in U.S. Pat. Nos. 4,545,389 and 4,683,894, or may comprise tiny silicon chips with a movable diaphragm etched into the chip. The diaphragm divides the pressure transducer into two chambers, one of which is referred to as the patient side chamber and contains the liquid within the liquid column to the patient. The other chamber is vented to atmosphere such that pressure readings taken of blood pressure from the patient side of the diaphragm are absolute values.

The diaphragm and thus the pressure transducer therefore flexes to provide readings of blood pressure based upon the differential pressure between the patient chamber and the vented chamber. The transducer then electronically senses the amount of flexing of the diaphragm or chip and translates the amount of flex into an electrical signal that is provided to a electronic monitor that reads out the patient's blood pressure for the attending personnel.

Because the reading is based upon the flexing of a diaphragm or other member separating the patient side chamber from the vent side chamber, it is important that the diaphragm have a zero reading when the two pressures are equal, that is, when the differential pressure between the chambers is zero. Due to manufacturing constraints, and due to the relatively low cost of such disposable pressure transducers, such pressure transducers are manufactured with a zero offset, that is, when the differential pressure is zero, there is some flexure to the diaphragm and therefore the electronic monitor would not read zero pressure for pressure transducers without some compensation.

Accordingly, before use, it is necessary to determine the particular zero offset for each pressure transducer and adjust the electronic monitor to take that offset into account and to insure that the monitor gives a true reading of zero when both chambers within the transducer opposing the diaphragm are at equal pressures.

Typically, the zero offset is determined by venting the patient side chamber to atmospheric pressure. When it is so vented, therefore, both chambers on either side of the diaphragm are at the same pressure, atmospheric, and any reading then present based on flexure of the diaphragm is the zero offset.

As a convenient means of venting the patient side or chamber to atmospheric pressure, the pressure transducer is normally supplied with a two-position stopcock where, in one position, the patient chamber is connected to the patient catheter and in the other position, the patient is cut out and the patient side chamber is vented to atmosphere through a side port of the stopcock having a standard female Luer fitting.

The venting side port of the stopcock is fitted with a deadender cap and the cap is removed during the venting procedure and reapplied after the zero offset has been determined. One of the problems in such operation, however is that the deadender cap is quite small and is easily dropped during or after its removal while the operator is taking the zero reading and whose attention therefore is diverted elsewhere.

Once dropped the cap is no longer sterile and the user must locate and affix another sterile deadender cap to the vent port in order to further use the pressure transducer with a patient.

Alternatively, the open end of the female Luer fitting of the vent port in the stopcock is uncovered during the zeroing procedure and thus can be touched by a non-sterile object and its sterility breached. In either event, the procedure is delayed and is inconvenient for the user.

In transit, a dust cap is generally fitted over the side port vent Luer fitting and thus an extra part is needed in the sterile package since in use, the dust cap is removed and the deadender, supplied in the same package applied.

SUMMARY OF THE INVENTION

In accordance with the present invention a captive deadender cap is provided for use with the female Luer side vent port fitting of the stopcock used to vent the patient side chamber within the pressure transducer. As such the captive deadender cap is affixed loosely to the female Luer fitting prior to shipment and the use of a dust cap is eliminated. In use, the captive deadender cap may be loosened to provide the venting of the patient chamber and then retightened after the zero offset has been obtained and the electronic instrument adjusted to take the offset in to consideration.

Thus the captive deadender cap is never removed during the venting operation and thus there is no danger of the cap being dropped or misplaced and the sterility of the female Luer fitting is not easily compromised.

In producing the captive deadender cap of the present inventions preferably a plurality of retention tabs are formed at the interior surface of the captive deadender cap aligned with the normal internal threads and located adjacent to the open end of the captive deadender cap, that is, the end that is screwed on to the female Luer fitting. The other end of the captive deadender cap is, of course, closed. The retention tabs are shaped such as to not readily enter the external screw threads of the female Luer fitting of the vent port of the stopcock. Thus the captive deadender cap cannot easily be unscrewed from the female Luer fitting. The shape of the retention tabs are, however, shaped such that a user, with fairly little additional force, can overcome the reluctance of the retention tabs to enter the external screw threads so that the user can, if desired, readily remove the captive deadender cap.

DESCRIPTION OF THE PREFERRED EMBODIMENT

Figure 1:
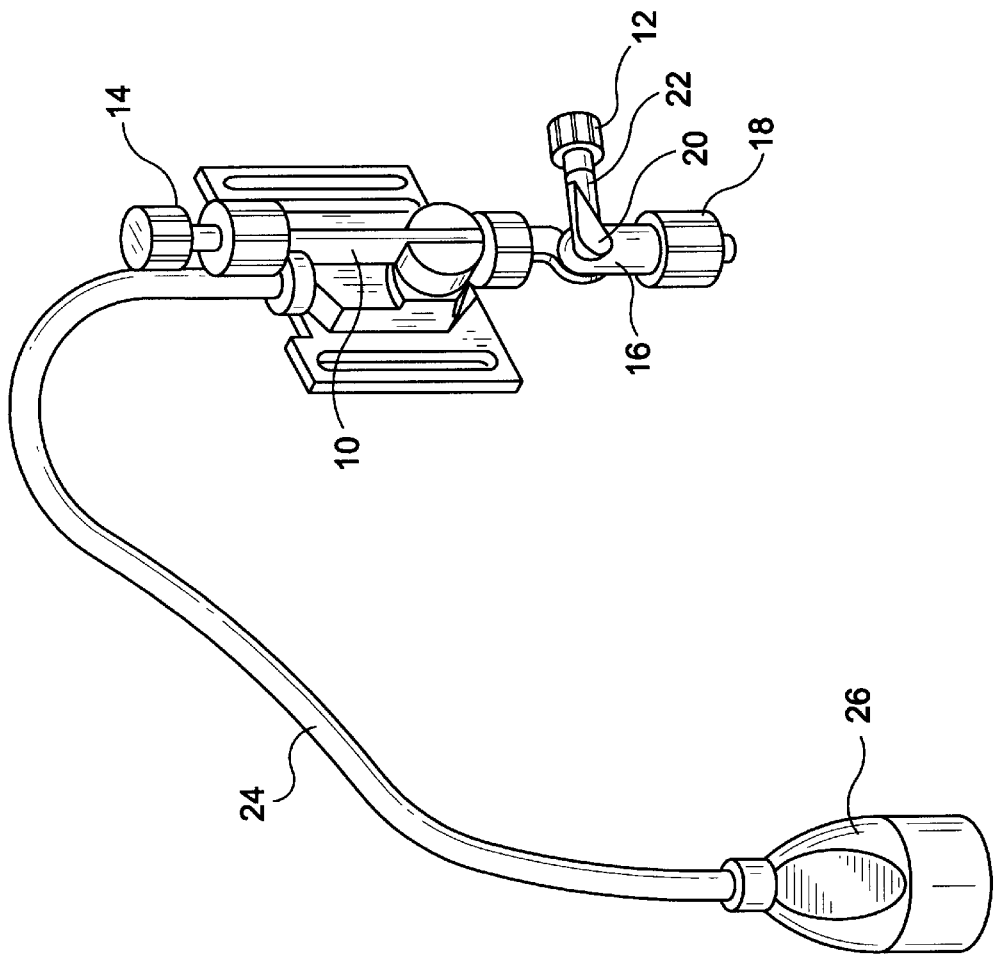
FIG. 1 is an isometric view of a disposable pressure transducer having a captive deadender cap constructed in accordance with the present invention.

Referring now to FIG. 1, there is shown an isometric view of a disposable pressure transducer 10 having affixed thereto, a captive deadender cap 12 constructed in accordance with the present invention. As with conventional disposable pressure transducer, the disposable pressure transducer 10 includes a housing within which is positioned a flexure means preferably a diaphragm and which separates the housing into a pair of chambers, one of which is the patient side chamber and the other chamber is vented to atmosphere.

The patient side chamber is in the liquid column path that communicates between a reservoir of sterile liquid and the catheter that is placed within the patients bloodstream and therefore the patient side chamber sees the pressure within that bloodstream. As noted the construction may by of the type shown and described in the aforementioned U.S. Pat. Nos. 4,454,389 and 4,683,894.

An inlet port 14, preferably in the form of a Luer fitting is normally provided in the disposable pressure transducer 10 and is a connection for the incoming sterile liquid through a flexible tubing that ultimately connects to a reservoir of that liquid, not shown. As stated the incoming liquid and therefore the inlet port 14 lead directly into the patient side chamber within the disposable pressure transducer 10. On the opposite side of the disposable pressure transducer 10 there is a two position stopcock 16 that also communicates with the patient side chamber.

The stopcock 16 has an outlet port 18, again in the form of a Luer fitting that is adapted to communicate with a flexible tubing leading, eventually to a catheter having an open end positioned within the particular blood vessel of the patient. Stopcock 16 is movable between its two positions by means of a lever 20. In one position of the stopcock 16, not the one shown in FIG. 1, the liquid from the reservoir communicates directly to the patient through the inlet port 14, the patient side chamber and the outlet port 18.

In the position of the stopcock 16 as indicated by lever 20 in FIG. 1, a vent port 22 on the stopcock 16 communicates with the patient side chamber within disposable pressure transducer 10 and is used to vent the patient side chamber to atmosphere to zero the electronic instrument not shown.

As will be seen the vent port 22 is a female Luer fitting and is covered by captive deadender cap 12. An electrical cable 24 depends from the disposable pressure transducer 10 ending in a special plug 26 for connection to the electronic monitor for providing a visual readout of the various detected parameters such as systolic and diastolic blood pressures.

Figure 2:
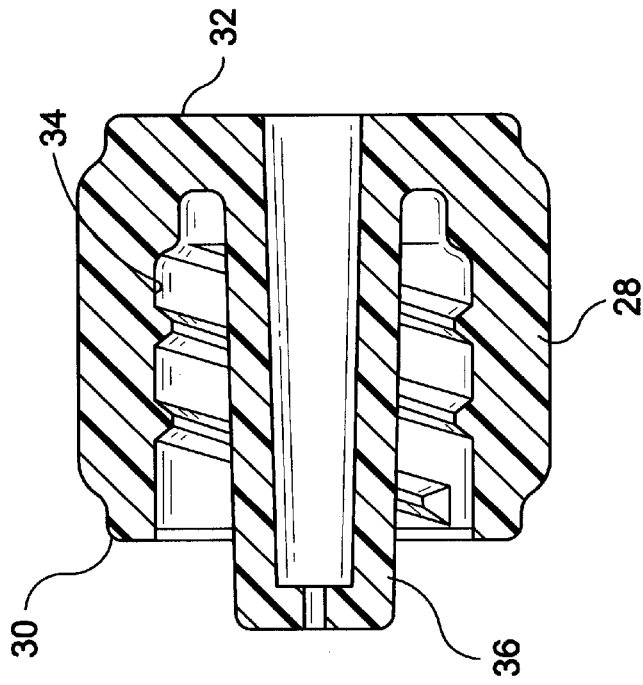
FIG. 2 is a side cross-sectional view of a typical prior art deadender currently used with disposable pressure transducers.

Accordingly when the stopcock 16 is in the position as shown in FIG. 1, the patient side chamber is vented to atmospheric, and, since the vent side chamber is normally vented to atmospherics the pressures on both sides of the diaphragm are equal and the operator can determine the zero offset and make the necessary correction to the electronic instrument to negate that offset. Obviously, the zero offset is determined before each disposable transducer is used and there may be occasion to recheck the zero offset after some period of use to see if the transducer has experienced drift and a new zero offset determined and the instrument rezeroed. Turning now to FIG. 2, there is shown a side cross-sectional view of a typical deadender vent cap that is a one piece injection molded unit of a high impact plastic such as acrylonitrile-butadiene-styrene (ABS) and includes an outer cylindrical flange 28 having an open end 30 which is screwed on to the female Luer fitting of vent port 22 and a closed end 32. The cylindrical flange 28 has internal threads 34 in order to be screwed on to the female Luer fitting of the vent port 22. A cylindrical projection 36 is formed within the cylindrical flange 28 depending outwardly from the closed end 32. Cylindrical projection 36 extends outwardly from open end 30 a predetermined length.

As can readily be seen, when the deadender vent cap of the prior art is screwed on to a female Luer fitting of vent port 22, it will close off the internal passage of the vent port 22. When unscrewed and removed, the cylindrical projection 36 withdraws from the internal passage of the female Luer fitting of vent port 22 and the patient side chamber within the disposable pressure transducer is open to atmospheric pressure through the vent port 22 of stopcock 16.

Figure 3:
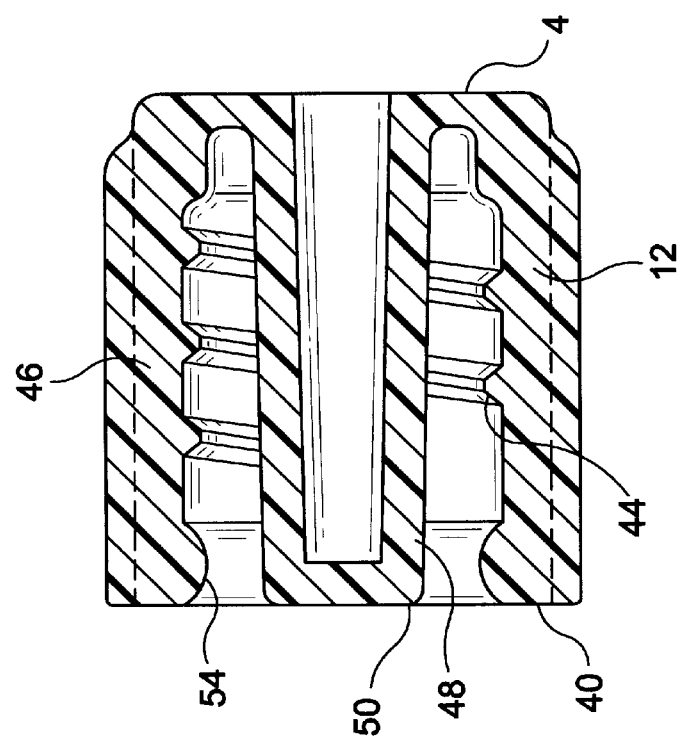
FIG. 3 is a side cross-sectional view of a captive deadender cap constructed in accordance with the present invention.
Figure 4:
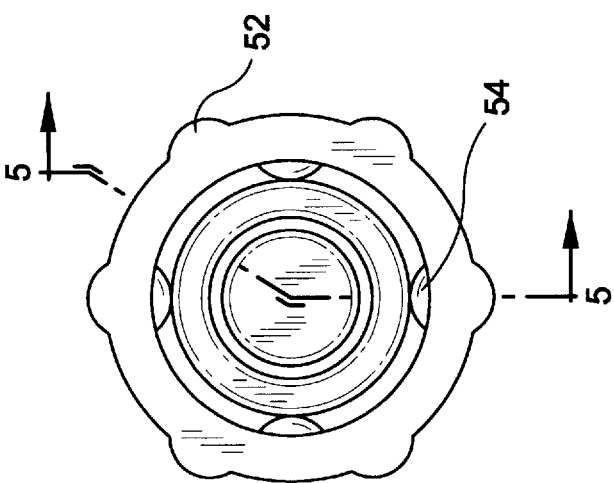
FIG. 4 is an end view of the captive deadender cap shown in FIG. 3.

Turning now to FIGS. 3 and 4 there is shown in FIG. 3 a side cross-sectional view of a captive deadender cap 38 constructed in accordance with the present invention and in FIG. 4, an end view of the captive deadender cap 38 of FIG. 3. The captive deadender cap 38 has an open end 40 that is adapted to be screwed on to the female Luer fitting of vent port 22 (FIG. 1.) and a closed end 42. Internal threads 44 are formed in an outer cylindrical flange 46 and the threads are of a standard pitch and configuration so as to mate complementary with the external threads of a standard female Luer fitting.

An internal projection 48 extends outwardly from closed end 42 toward the open end 40 of captive deadender cap 38, however as can be noted in FIG. 3, the outer cylindrical flange 46 has been extended as contrasted with the prior art deadender cap of FIG. 2 such that the internal projection has its free end 50 ending in approximately the same plane as the open end 40 of captive deadender cap 389 the purpose of which will be evident.

Captive deadender cap 38 also may include a plurality of ridges 52 formed on the exterior surface of the outer cylindrical flange 46 in order to facilitate the gripping by a user to twist the captive deadender cap 38 during screwing or unscrewing the same to the female Luer fitting on the vent port 22 (FIG. 1).

Finally a plurality of retention tabs 54 are formed on the interior of the outer cylindrical flange 46 and are generally in alignment with the internal threads 44 however the profile of the retention tabs 54 are different than the profile of the standard Luer lock internal threads 44 of captive deadender cap 12.

The retention tabs 54, four are shown, are positioned adjacent the open end 40 of the captive deadender cap 12 and are formed having a radius that is sufficiently large that the retention tabs 54 do not easily enter the external screw threads of a standard female Luer fitting and therefore resistance is encountered in attempting to unscrew the captive deadender cap 12 completely off of the female Luer fitting of vent port 22 (FIG. 1).

Figure 5:
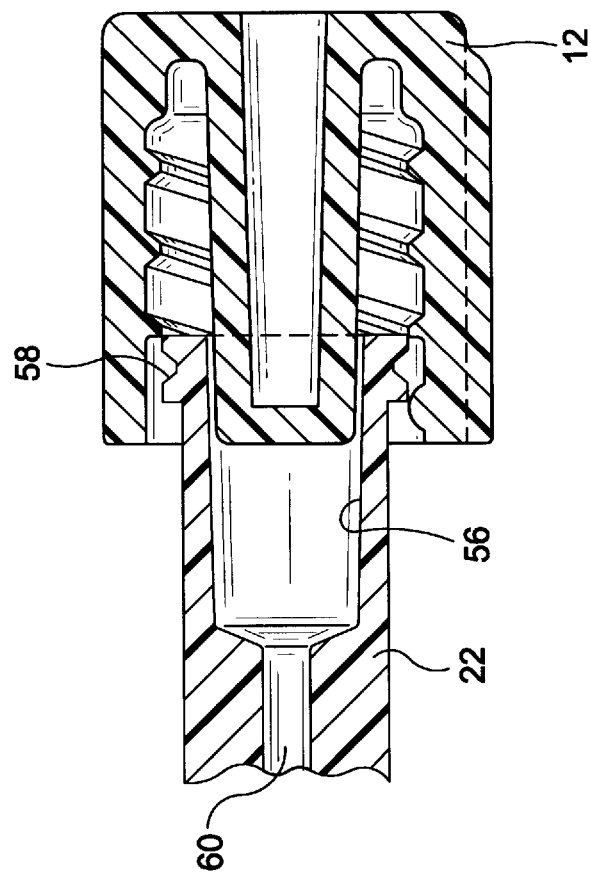
FIG. 5 is a cross-sectional view taken along the lines 5—5 of FIG. 4 of a captive deadender cap of the present invention positioned on a standard female Luer fitting.

The difference in the threads can be seen in FIG. 5 showing a cross sectional view of the captive deadender cap 12 affixed to the standard female Luer fitting of the vent port 22. As can be seen in FIG. 59 the female Luer fitting of vent port 22 includes the standard internal passage 56 having the Luer angle and has, at its distal end, external screw threads 58 to provide a threaded engagement to a deadender cap having a standard male Luer fitting. A further passageway 60 provides communication with the main body of the stopcock 16 (FIG. 1) and thence of course to the patient side chamber of the disposable pressure transducer 10.

The standard thread profile of the Luer fittings includes a thread angle A of about 60 degrees, a thread depth of about 0.025 inches, and a width at the base of the threads at B of about 0.007 inches. In contrast, the retention tabs 54 are preferable arcuate and formed as arcs of a circle having a radius of about 0.040 inches and have a thread depth of about 0.020 inches. Thus, the retention tabs 54 have about the same thread depth as the standard internal threads but the larger radius profile of retention tabs 54 prevents the retention tabs 54 from easily entering the external threads 58 of the standard female Luer fitting of vent port 22. Instead, resistance is encountered in trying to completely unscrew the captive deadender cap 12 to separate it from the vent port 22.

Accordingly, the captive deadender cap 12 remains captive on the vent port 229 yet, by unscrewing it to the position of FIG. 59 there is sufficient withdrawal of the internal projection 48 from the Luer internal passage 56 so as to vent the passage 60 and thus, the stopcock 16 to the patient side chamber within disposable pressure transducer 10. By tightening the captive deadender cap 12, however, the internal projection 48 reenters the Luer internal passage 56 to seal off the vent port 22.

Thus by twisting the captive vent cap 12, the vent port 22 can vent the patient side chamber of the disposable pressure transducer 10 to atmosphere or discontinue such venting.

Due also to the circular profile of retention tabs 54, with an increase in the normal torque required in unscrewing the captive deadender cap 12, the slight increased resistance may be overcome and the retention tabs 54 will pass along the external threads 58 so that the user may fully remove the captive deadender cap 12 if so desired.

Thus, although captive deadender cap 12 will not vibrate free of the vent port 22 or be easily removed, the slight added resistance to the retention tabs 54 being unscrewed through external screw threads 58 can be sensed by the user but can, at will, be overcome in the event the user wants to completely remove the captive deadender cap 12.

It will be understood that the scope of this invention is not limited to the particular specific embodiment disclosed herein, by way of example, but only by the scope of the appended claims, including their equivalents.

I claim:

1. A venting and deadender device adapted to be threadedly engaged to a standard medical female Luer fitting having standard external threads and an opening for the passage of a fluid, said venting and deadender device having internal threads complementary to the external threads of the female Luer fitting and having an open end adapted to be screwed onto the female Luer fitting, said venting and deadender device having an internal projection adapted to enter and close off the opening in the female Luer fitting when said venting and deadender device is fully screwed on to the female Luer fitting and to vent the opening when said venting and deadender device is unscrewed from the female Luer fitting, said venting and deadender device having a plurality of retention tabs formed adjacent to said internal threads and adjacent the open end of said venting and deadender device, said venting and deadender device having its length of screw threads such that said venting and deadender device can be unscrewed fully from the external threads of the female Luer fitting while said retention tabs retain said venting and deadender device on and freely rotatable with respect to the female Luer fitting, said retention tabs being dimensioned so as to allow said venting and deadender device to be readily removed from said female Luer fitting by overcoming slight resistance by the user to move said retention tabs over the external threads of the female Luer fitting.

2. In a medical pressure transducer, the improvement of claim 1 wherein said retention tabs comprise arcuate tabs having a thread depth about the same as the threads of a standard Luer fitting.

3. In a medical pressure transducer, the improvement of claim 2 wherein said arcuate tabs are formed as arcs of a circle having a predetermined radius.

4. In a medical pressure transducer, the improvement of claim 3 wherein said radius of said arcuate tabs is about 0.040 inches.

* * * * *